United States Patent
Bruce et al.

(10) Patent No.: US 7,955,613 B2
(45) Date of Patent: Jun. 7, 2011

(54) BIOARTIFICIAL IMPLANT AND ITS USE AND METHOD OF REDUCING THE RISK FOR FORMATION OF CONNECTIVE TISSUE AFTER IMPLANTATION

(75) Inventors: Adam Bruce, Viken (SE); Lars Bruce, Viken (SE); Bo Nilsson, Uppsala (SE); Olle Korsgren, Uppsala (SE)

(73) Assignee: Tikomed AB, Viken (SE)

( * ) Notice: Subject to any disclaimer, the term of this patent is extended or adjusted under 35 U.S.C. 154(b) by 984 days.

(21) Appl. No.: 10/574,114

(22) PCT Filed: Oct. 4, 2004

(86) PCT No.: PCT/SE2004/001418
§ 371 (c)(1),
(2), (4) Date: Mar. 31, 2006

(87) PCT Pub. No.: WO2005/030283
PCT Pub. Date: Apr. 7, 2005

(65) Prior Publication Data
US 2006/0263405 A1   Nov. 23, 2006

(30) Foreign Application Priority Data
Oct. 2, 2003 (SE) .......................................... 0302599

(51) Int. Cl.
*A61F 2/00* (2006.01)
(52) U.S. Cl. .................. 424/423; 604/890.1; 623/23.72; 424/195.17
(58) Field of Classification Search .................... 424/423
See application file for complete search history.

(56) References Cited

U.S. PATENT DOCUMENTS

| | | | |
|---|---|---|---|
| 4,752,294 A | | 6/1988 | Lundgren |
| 5,387,327 A | * | 2/1995 | Khan ............................ 600/347 |
| 5,693,514 A | | 12/1997 | Dorian et al. |
| 5,782,912 A | | 7/1998 | Brauker et al. |
| 5,800,828 A | | 9/1998 | Dionne et al. |
| 5,843,069 A | | 12/1998 | Butler et al. |
| 5,876,742 A | | 3/1999 | Cochrum et al. |
| 5,913,998 A | | 6/1999 | Butler et al. |
| 6,083,523 A | | 7/2000 | Dionne et al. |
| 6,372,244 B1 | * | 4/2002 | Antanavich et al. .......... 424/423 |
| 7,527,804 B2 | | 5/2009 | Närhi et al. |
| 7,547,471 B2 | | 6/2009 | Bjursten et al. |
| 2003/0050689 A1 | * | 3/2003 | Matson ........................ 623/1.15 |
| 2003/0108590 A1 | * | 6/2003 | Peery et al. .................... 424/424 |
| 2003/0153981 A1 | * | 8/2003 | Wang et al. ................. 623/22.21 |
| 2009/0292191 A1 | | 11/2009 | Bjursten et al. |

FOREIGN PATENT DOCUMENTS

| | | |
|---|---|---|
| EP | 1476203 | 11/2004 |
| JP | 10-503964 | 4/1998 |
| RU | 2040277 | 7/1995 |
| RU | 2109495 | 4/1998 |
| RU | 2113830 | 6/1998 |
| RU | 2117456 | 8/1998 |
| RU | 2142867 | 1/2000 |
| RU | 2157245 | 10/2000 |
| RU | 2185127 | 7/2002 |
| RU | 2191607 | 10/2002 |
| SU | 209642 | 1/1968 |
| WO | WO 0170379 A1 * | 9/2001 .......................... 63/6 |
| WO | WO 01/78906 A1 | 10/2001 |
| WO | WO 02/02745 A2 | 1/2002 |
| WO | WO 03063925 | 8/2003 |

OTHER PUBLICATIONS

LaVan et al., Small-scale systems for in vivo drug delivery, Nature Biotechnology, 2003, vol. 21, p. 1184-1191.*
Okazaki et al., New Ti Alloy without Al and V for Medical implants, Advanced Engineering Materials, vol. 2, No. 5, 2000 p. 278-281.*
Indian Office Action in corresponding Indian Appl. No. 1914/DELNP/2006 dated Sep. 16, 2008.
Belorussian Office Action dated Jan. 13, 2009 in corresponding Application No. 20060401, with English translation.
Melikyan et al., *Technical Physics Letters*, vol. 28, No. 8, pp. 673-674 (2002).
Piskin, *The International Journal of Artificial Organs*, vol. 25, No. 5, pp. 434-440 (2002).
International Search Report (PCT/ISA/210), Jan. 3, 2005.
Japanese Office Action dated Nov. 5, 2010 with English translation for corresponding Japanese Patent Application No. 2006-532233.

(Continued)

*Primary Examiner* — Jon P Weber
*Assistant Examiner* — Tiffany M Gough
(74) *Attorney, Agent, or Firm* — Harness, Dickey & Pierce, P.L.C.

(57) ABSTRACT

A bioartificial implant comprises a semipermeable barrier designed from one side to allow diffusion or prevent diffusion of predetermined substances/materials/molecules/cells/cell lines produced in the human body to the other opposite side of the barrier, and from said other opposite side to allow diffusion or prevent diffusion of predetermined substances which are the same as or different from the first mentioned substances/materials/molecules/cells/cell lines. The semipermeable barrier has a surface coating at least on said one side a bioactive metal, such as titanium, which surface coating is permeable to allow said diffusions. In a method for reducing the risk of formation/growth of connective tissue in connection with an implant which comprises a semipermeable barrier, the barrier is provided at least on one side with a permeable coating of bioactive metal. An example of the use of the implant is bioartificial pancreas.

12 Claims, 12 Drawing Sheets

OTHER PUBLICATIONS

Shinji Sakai, et al., "Evaluation of Performance of Aminosilica-Titania Membrane As Cell-Encapsulated Immunoisolative Membrane," Proceedings of the Meeting of the Society for Biotechnology, Japan (2001), Aug. 24, 2001, p. 201.

* cited by examiner

Membrane TF-200

Versapor® 200

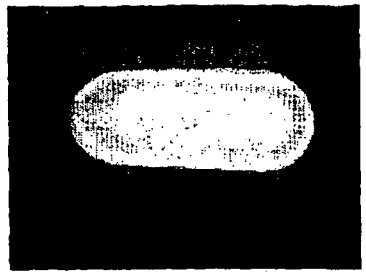 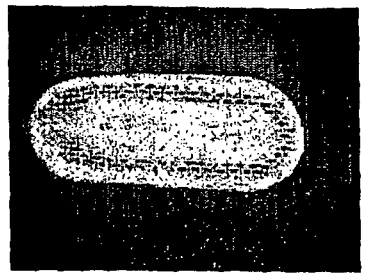 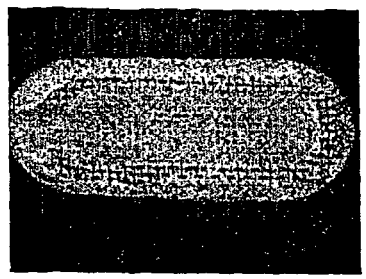
Fig. 8b    Fig. 8c    Fig. 8d
 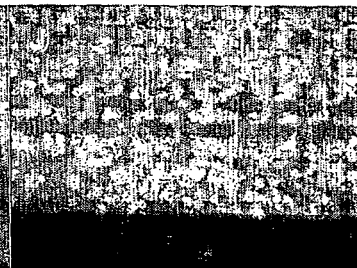 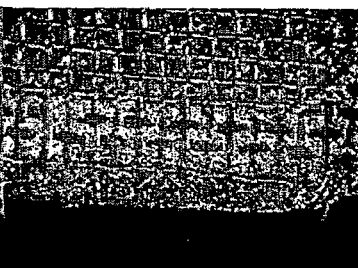
Fig. 8e    Fig. 8f    Fig. 8g
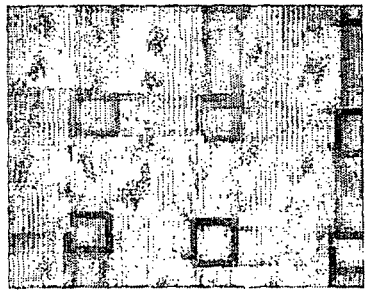 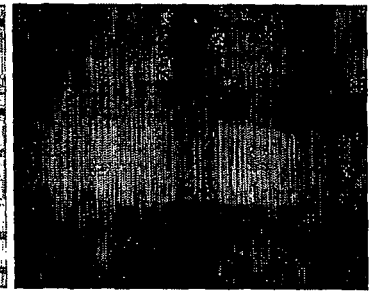 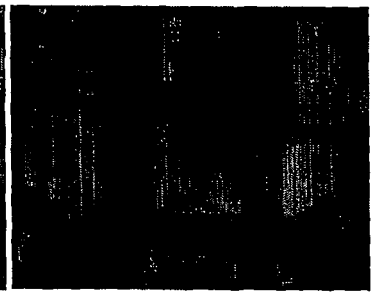
Fig. 8h    Fig. 8i    Fig. 8j
  
Fig. 8k    Fig. 8l    Fig 8m

BIOARTIFICIAL IMPLANT AND ITS USE AND METHOD OF REDUCING THE RISK FOR FORMATION OF CONNECTIVE TISSUE AFTER IMPLANTATION

CROSS-REFERENCE TO RELATED APPLICATIONS

This application claims priority under 35 USC §119 to PCT Application No. PCT/SE2004/001418, filed on Oct. 4, 2004, and Swedish Application No. 0302599-6, filed on Oct. 2, 2003, in the Swedish Patent and Registration Office (PRV), the entire contents of which are incorporated herein by reference.

FIELD OF THE INVENTION

The technical field of the present invention involves bioartificial implants based on a semipermeable barrier.

BACKGROUND OF THE INVENTION

It is known in the organ transplantation technique that the human body opposes transplantation of an organ/tissue by rejection phenomena caused by the immune defense of the body. In order to avoid immunosuppressive medicaments (secondary effects, impairment of the immune defense) bioartificial implants have been developed which comprise donor tissue/cells which are to be implanted and a semipermeable barrier or "filter" which is to allow diffusion of nutrients and oxygen from the donee's body to the implanted (i.e. transplanted) donor tissue/cells, but no diffusion of the donee's immune defense mechanisms (cells), while at the same time it shall allow diffusion of desirable substances produced by the donor tissue/cells to the donee's body. Examples in the patent literature concerning such bioartificial implants include U.S. Pat. No. 6,632,244 and WO 02/02745, which discuss particularly implantation of isolated islets of Langerhans (bio-artificial pancreas) for production of insulin in the donee's body. U.S. Pat. No. 6,632,244 also discusses the risk of fibrosis (growth of connective tissue) in the donee's body, which results in the pores of the barrier being covered by connective tissue, whereby the implant "starves to death" (hypoxia), since it does not receive oxygen and nutrients from the donee's body. This phenomenon occurs in barrier materials which are not biocompatible. According to the latter patent, this inconvenience is avoided with a biocompatible implant in the form of a thin sheet of three components (a) a core, which consists of living tissue, trophic factors and nurse cells, an alginate polymer crosslinked with, for instance, calcium, and a fiber net for strength, (b) a coating of alginate polymer crosslinked with calcium for control of permeability, and (c) a coating which also consists of crosslinked alginate polymer. It is recommended that the thickness of the implant not exceed 400 μm.

A transplant which is also coated with alginate (multilayer) is disclosed in U.S. Pat. No. 5,876,742. The coating is said to be non-fibrogenic. The thickness of the coating is 20-200 μm.

U.S. Pat. No. 5,782,912 discloses an implant with a wall consisting of a first porous membrane, which is proximal to the donee's tissue and which is said to favor formation of vascular structures in a donee membrane interface and there prevent formation of connective tissue. The implant also has a second porous membrane, which forms an immuno-isolated space. The space encloses tissue, pancreas islets, which must be protected from being contacted by the donee's cells. The second membrane allows diffusion of components which are generated by the enclosed tissue, producing insulin for instance. The second membrane also allows diffusion of nutrient from the donee to the space in order to provide the tissue with nutrient. The membranes are made of polymer, and the first membrane has a special three-dimensional pore structure. This patent publication states that "Known biocompatible medical implants are composed of ceramics and metals. Assuming these materials could be manipulated to provide the three-dimensional structures described herein, they would also be useful in the present invention".

U.S. Pat. No. 5,782,912 also discloses use of the device as a coating on an indwelling sensor and on an indwelling catheter, as means for transport of physiological factors to indwelling sensors, as means for transport of drugs from a chamber or catheter to donee tissue and as means for encapsulation of grafted cells for treatment of cellular and molecular deficiencies (immunoisolation).

The above-described implants and other implants based on semipermeable barriers are complicated in design and difficult to produce. There is reason to believe that these circumstances do not result in well-reproducible implants with the desired properties. There is also reason to believe that the vascularising barrier of the known implants is not optimally efficient to prevent fibrosis since a liquid-filled gap between connective tissue and barrier is not taken into consideration.

OBJECT OF THE INVENTION

An object of the invention is to provide such a bio-artificial semipermeable implant of the type described above, i.e. having the property of being vascularising, inhibiting growth of connective tissue (fibrosis), being simpler in design and easier to produce than the known implants.

SUMMARY OF THE INVENTION

The object is achieved by an implant having the features in claim 1 and a method according to claim 9. Advantageous embodiments have the features defined in the dependent claims.

The invention is based on our surprising discovery that if a conventional semipermeable barrier, "filter", "membrane", adapted to be implanted in the human body and being capable of selectively letting nutrient, oxygen, other gases, tissue/cell substances, cell lines, but no immune defense mechanisms diffuse therethrough, is provided with a permeable coating of biocompatible or bio-active metal, the fibrosis problem will be eliminated significantly.

Experiments performed give us reason to believe that this fibrosis counteracting effect results from the fact that blood vessels in the donee, in which the barrier with the bioactive coating is implanted, are "attracted" to the surface of the coating and grow along the same. As a result, the growth of connective tissue, fibrosis, close to this surface will be blocked, and such growth of connective tissue will not have time to start again before the blood vessels grow close to the surface of the bioactive coating. Blood vessels and growth of blood vessels close to the surface of the bioactive coating result in turn in the fact that nutrient and oxygen from the blood vessels can be transported (diffuse) through the implant unimpeded by connective tissue.

"Attraction" should here not be interpreted as a strictly scientific expression since the mechanism behind the effect has not yet been established. The expression rather means to establish the fact that, according to our findings, blood vessels do not grow (grow insufficiently) to and close to the surface of a conventional barrier—referred to as biocompatible or not— while blood vessels do so close to such a coating on a conventional barrier consisting of bioactive metal.

It should be noted that the metal coating is not to be considered a semipermeable barrier in addition to the conventional semipermeable barrier on which the metal is deposited. This is contrary to the alginate layer or polymer membrane in the patents mentioned above, which adds a vascularising, fibrosis-inhibiting effect to the underlying semipermeable barrier or membrane. The alginate/polymer layer is semipermeable itself and produces permeability of the implant which is a permeability different from that of the underlying semipermeable barrier. The metal coating of an implant according to the invention does not have such an effect.

BRIEF DESCRIPTION OF THE DRAWINGS

FIG. 8b is a light microscopy photography of a TheraCyte™ device without any titanium coating;

FIG. 8c is a light microscopy photography of a TheraCyte™ device with one titanium layer;

FIG. 8d is a light microscopy photography of a TheraCyte™ device with two titanium layers;

FIGS. 8e, 8h, 8k are magnifications of the TheraCyte™ device illustrated in FIG. 8b;

FIGS. 8f, 8i, 8l are magnifications of the TheraCyte™ device illustrated in FIG. 8c;

FIGS. 8g, 8j, 8m are magnifications of the TheraCyte™ device illustrated in FIG. 8d;

EMBODIMENTS OF THE INVENTION

Semipermeable Barrier

Figure 1:
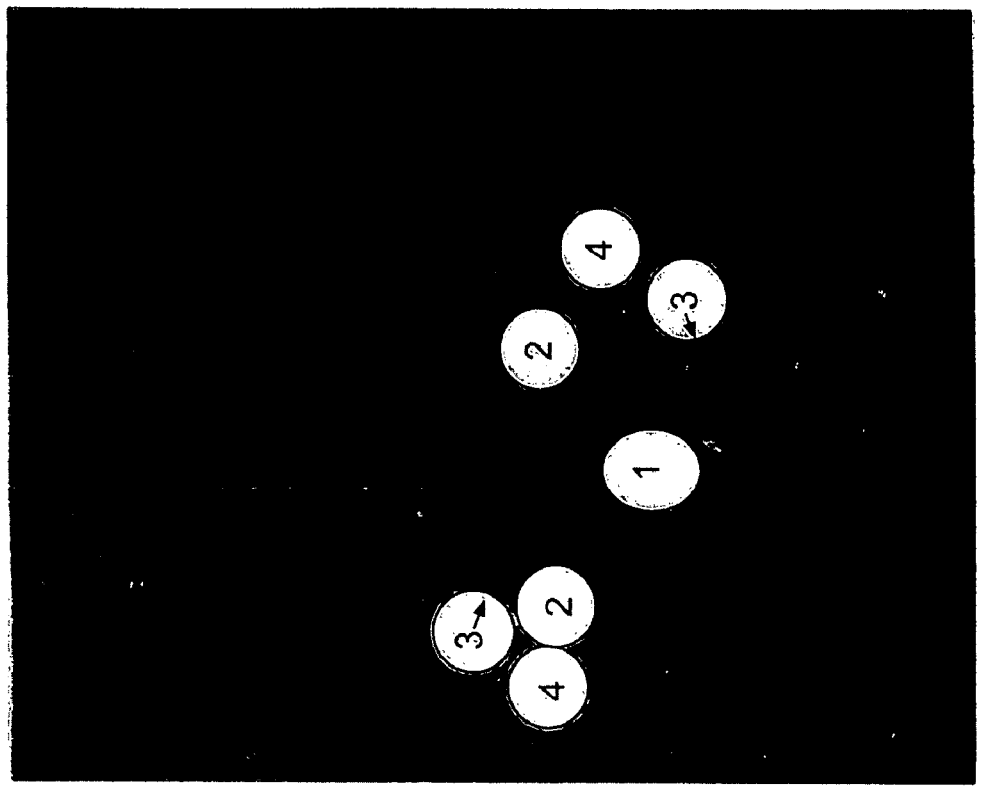
FIG. 1 is a light microscope photography illustrating a conventional implant comprising islets of Langerhans embedded in an alginate barrier, which implant is in a transplanted state.

The semipermeable barrier of the implant, which barrier is made of a polymer material, with the above properties regarding the above-mentioned transports can be of a prior-art type, for instance according to the above-mentioned U.S. Pat. No. 6,372,244, or some other material of a tissue-compatible kind, for instance GoreTex®. Semipermeable barriers of other materials, such as carbohydrates, cellulose, plastic (for example polycarbonate), hydrogels, are already available on the market, marketed by, for instance, Millipore Inc, Baxter Inc, Amicon and Pall Corporation. They are marketed or, on request, produced with different pore sizes depending on what is to be blocked or let through. There are on the market, for instance, semipermeable barriers which block the diffusion of cells (immune defense), but let through molecules (nutrient and oxygen as well as substances from the donee's body in which the barrier is implanted) and substances from the donor's organ/organ part/tissue which is enclosed in the barrier to the donee's body, for instance insulin produced by the islets of Langerhans implanted in the donee's body. The barrier can be in the form of a sheet, in which tissue or cells to be implanted is/are embedded, or in the form of a container (bag, sleeve), in which cells/tissue to be implanted are/is enclosed. In this case, the bioactive coating is at least arranged on the outside of the container.

Bioactive Metal Coating and Deposition Thereof.

The bioactive metal coating of the implant should be permeable, i.e. have pores/openings letting through (diffusion) nutrient, oxygen and tissue/cell substances, i.e. the coating should not interfere with the function and purpose of the semipermeable barrier. However, the pore size need not prevent diffusion of the immune defense; this is taken care of by the semipermeable barrier. The permeability of the coating should thus be at least as great as that of the barrier (while taking into consideration the small effect of the metal coating on the pore walls of the semipermeable barrier). The coating may consist of powder/dust, deposited on the barrier by some prior-art atomizing process, or thin-film technique such as evaporation (PVD), sputtering, or be in the form of a net or a perforated (for instance by laser) foil which is attached in some suitable manner, for instance gluing to the barrier using a biological glue or laser welded thereto. Attaching the foil by sewing is also an acceptable method. "Sprinkling" of grains on the barrier is another option. When choosing a method for depositing the coating on the barrier, the character of the barrier material, especially temperature resistance, should of course be taken into consideration.

The coating should be substantially continuous, by which is meant that connective tissue should be prevented from growing on the underlying semipermeable barrier. While this requirement hardly creates problems if the coating consists of a foil, the requirement must be paid attention to if the coating is deposited on the semipermeable barrier using a method where the coating is composed of particles, deposited, for instance by sputtering, evaporation, chemical precipitation. Thus it must be ensured that the coating of bioactive material on the semipermeable barrier is even and without significant knots that could cause growth of connective tissue. On the other hand, it must also be ensured that the requirement for absence of knots in the coating does not lead to exaggeration in depositing so that the coating becomes excessively thick and, thus, clogs the pores in the semipermeable barrier.

It has been found that excellent results (transport as stated above and preventing of fibrosis) are achieved using today's depositing technique, with a thickness of the metal coating from about 5 nm and more, more preferably about 50-250 nm, independently of the pore size of the barrier.

With reference to that stated above it should be noted that, according to the invention, it cannot be excluded that particles of the bioactive material penetrate when being deposited into the pores/openings of the barrier, thus reducing them, as long as pores/openings remain for said transport or diffusions.

Bioactive Metal

By bioactive metal is meant biocompatible metal which in addition to biocompatibility is capable of—as mentioned above—"attracting" tissue and anchoring this to itself. Such materials are titanium, zirconium, tantalum and suitable alloys thereof, as is already known. According to the invention titanium is preferred.

EXAMPLE 1

Figure 2:
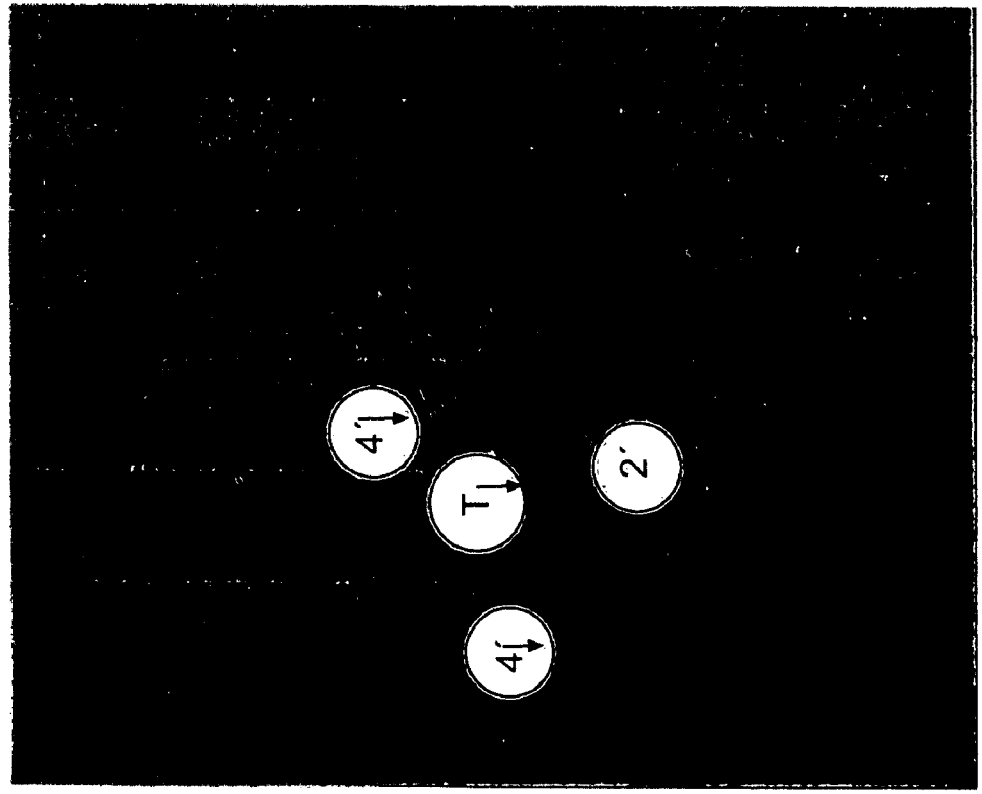
FIG. 2 is a light microscope photography illustrating an implant with a semipermeable barrier coated on one side with a titanium coating according to example embodiments.

The difference in terms of connective tissue growth in connection with an implant of a semipermeable barrier without a bioactive metal coating and, according to the invention, with a bioactive metal coating is illustrated in FIGS. 1 and 2.

FIG. 1 is a light microscope photography illustrating a conventional implant, comprising the islets of Langerhans 1 embedded in an alginate barrier 2, which implant is in a transplanted state. The layer designated 3 is identified as connective tissue. The photography shows that the connective tissue 3 is positioned close to the implant, between the implant and the donee's tissue/blood vessel 4.

FIG. 2 shows an implant which consists of a conventional semipermeable barrier 2' which on one side is, according to the invention, coated with a titanium coating T. The component designated 4' is identified as a blood vessel. This is positioned close to the titanium coating T and even penetrates slightly into the coating. There is no connective tissue between the blood vessel and the barrier. There are hardly any blood vessels at all on the other side of the barrier, which has no titanium coating.

EXAMPLE 2

Figure 3:
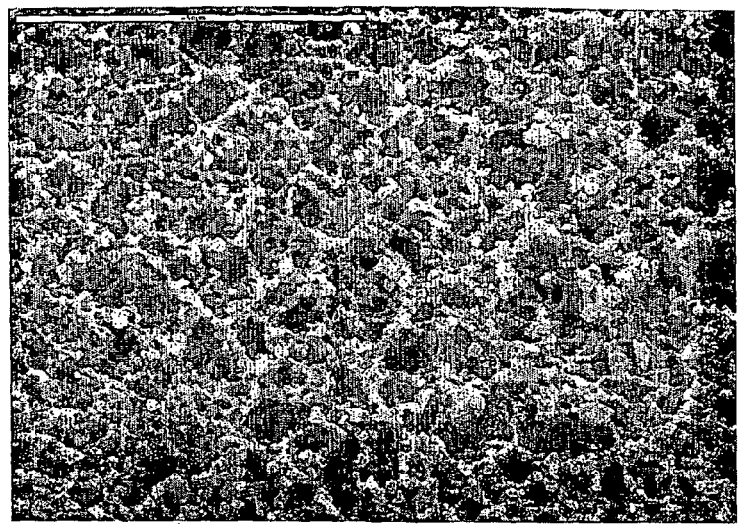
FIG. 3 is a photography illustrating a semipermeable barrier of cellulose coated with titanium using an evaporation technique according to example embodiments.

A titanium coating was deposited on one side of a semipermeable barrier of cellulose, consisting of Diaflo YM5 LOT AN 01383A from Amicon. The deposition occurred by evaporation technique in an evaporator from Edwards Inc. The coating was deposited with a thickness of 30 nm. The result is shown in FIG. 3 from which it is evident that the pores of the cellulose barrier are not clogged by the titanium particles, i.e. the surface structure of the barrier has not been substantially changed by the coating. FIG. 2 shows this barrier with a coating as an implant in a mouse, one month after implantation.

EXAMPLE 3

The Example was repeated using a filter from Millipore Inc, type SS 3.0 µm. The same results were obtained as in Example 1.

FURTHER ASPECTS ON THE INVENTION

The basic ideas of the invention are applicable not only to semipermeable barriers which enclose donor body tissue/cells to be transplanted in a donee, surviving there by supply of nutrient/oxygen from the donee's body. The inventive idea is also applicable to instruments, measuring elements etc which are to be inserted into the living body to allow transport of substances in general through a semipermeable barrier from opposite sides of the barrier wall. An example of such an application is a blood-sugar-detecting sensor with a semipermeable barrier round the sensor element which is implanted in the human body and connected to an insulin pump for delivering insulin according to the detected blood sugar content via an infusion set inserted in the body and also provided with a semipermeable barrier according to the invention. The inventive problem, i.e. preventing growth of connective tissue close to the barrier, is also in such cases solved by a permeable titanium coating as described above.

Examples of other applications of the invention are drug secretion (chemotherapy, analgesics etc), organ transplantation (kidney, liver etc), cells in bags producing erythropoeitin, coagulation factors, growth hormone, interferon α, parathormones, insulin etc, artificial organs (for instance liver cells), microdialysis technique.

It goes without saying that the invention is applicable to humans as well as animals.

The metal coating may consist of one or more separately deposited metal layers (foil or powder) and the titanium layer/layers can in the implant be in a sandwich construction with the barrier/barriers, if desired for selective transport of substances through the implant.

More Examples

EXAMPLES 4 and 5

Figures 4A, 4B, 4C:
FIG. 4a is a light microscope photography of a semipermeable membrane TF-200 without any coating.
FIG. 4b is a light microscope photography of a semipermeable membrane TF-200 coated with one titanium layer dry.
FIG. 4c is a light microscope photography of a semipermeable membrane TF-200 coated with one titanium layer wet.
Figures 5A, 5B, 5C:
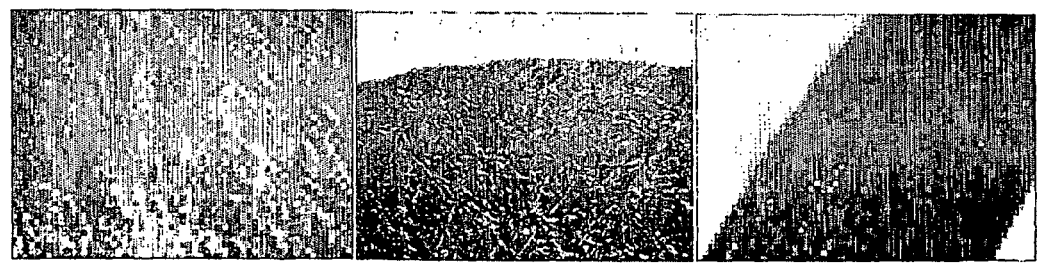
FIG. 5a is a light microscope photography of a semipermeable membrane Versapor® 200 without any coating.
FIG. 5b is a light microscope photography of a semipermeable membrane Versapor® 200 coated with one titanium layer dry.
FIG. 5c is a light microscope photography of a semipermeable membrane Versapor® 200 coated with one titanium layer wet.

FIGS. 4a-4c and 5a-5c illustrate studies on conventional semipermeable barriers (membranes) with the trade names TF-200 and Versapor®-200 from Pall Corporation. The structures of Ti-coated and non-coated membranes were investigated using a LEICA M76 microscope with an external light source. No change in structure could be detected when the membranes were coated with one Ti-layer compared to non-coated membranes. The membrane structure was also studied after incubation of the Ti-coated membranes in aqueous solution and no change was observed. The membrane structure was, thus, retained after both the coating procedure and the following exposure to aqueous solution. FIG. 4a illustrates membrane TF-200 without modification, that is without Ti-layer, FIG. 4b illustrates membrane TF200 coated with one Ti-layer dry, and FIG. 4c illustrates membrane TF-200 coated with one Ti-layer wet. FIG. 5a illustrates membrane Versapor® 200 without modification, that is without Ti-layer, FIG. 5b illustrates membrane Versapor® 200 coated with one Ti-layer dry, and FIG. 5c illustrates membrane Versapor® 200 coated with one Ti-layer wet.

EXAMPLES 6 and 7

Figure 6A:
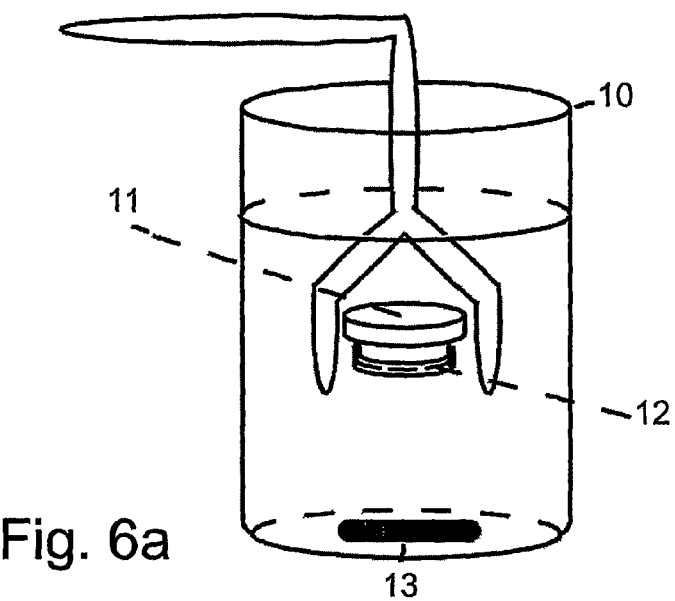
FIG. 6a schematically illustrates the set-up of a dialysis performance test.
Figure 6B:
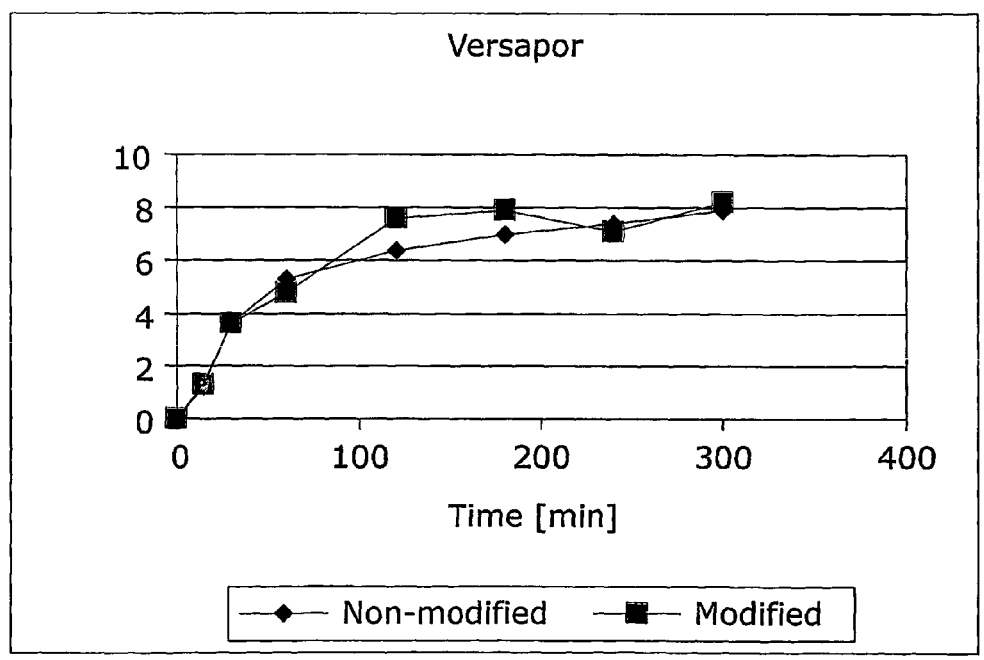
FIG. 6b is a diagram comparing dialysis of glucose through a Versapor® 200 membrane with or without titanium coating.
Figure 6C:
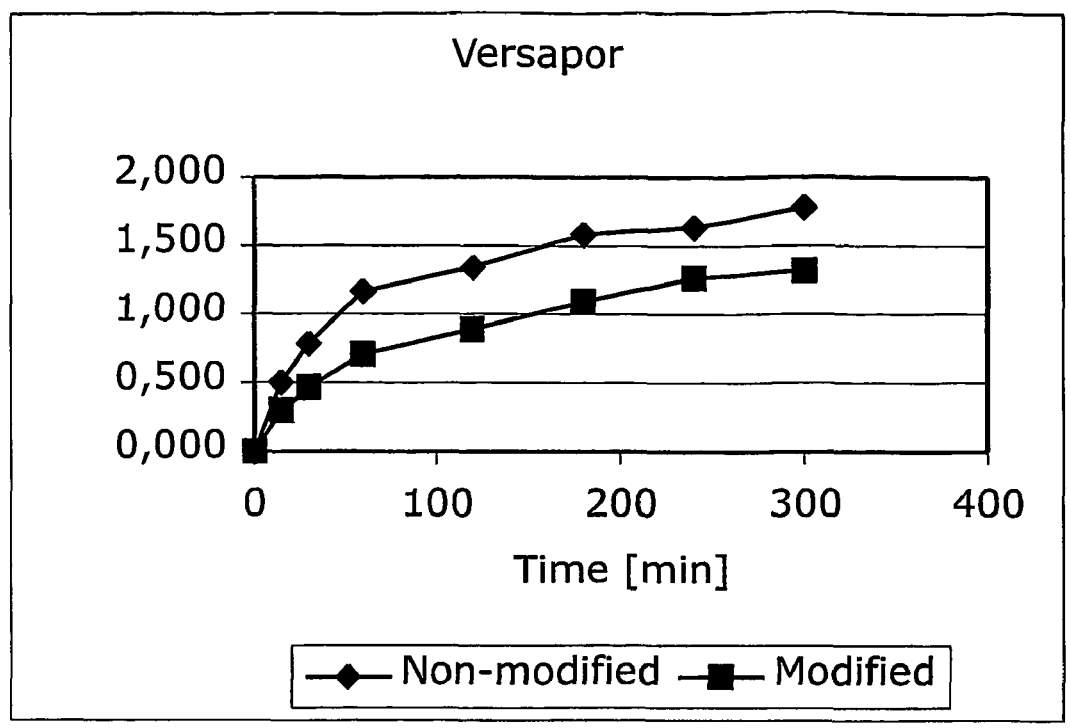
FIG. 6c is a diagram comparing dialysis of protein through a Versapor® 200 membrane with or without titanium coating.
Figure 6D:
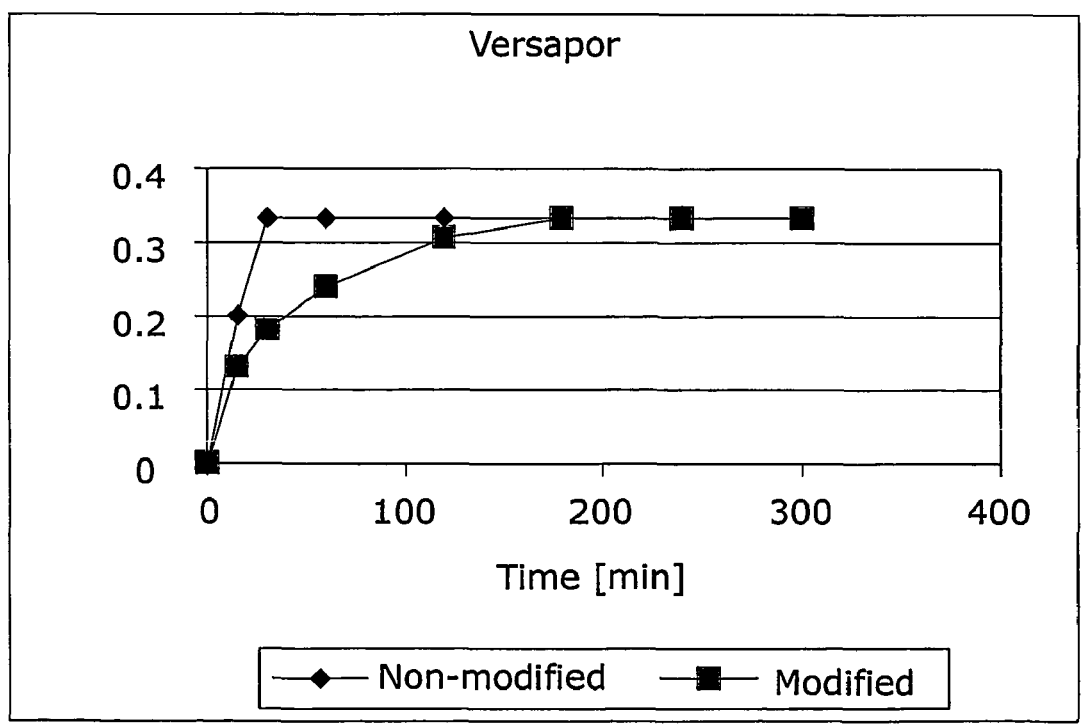
FIG. 6d is a diagram comparing dialysis of IgG through a Versapor® 200 membrane with or without titanium coating.
Figure 7A:
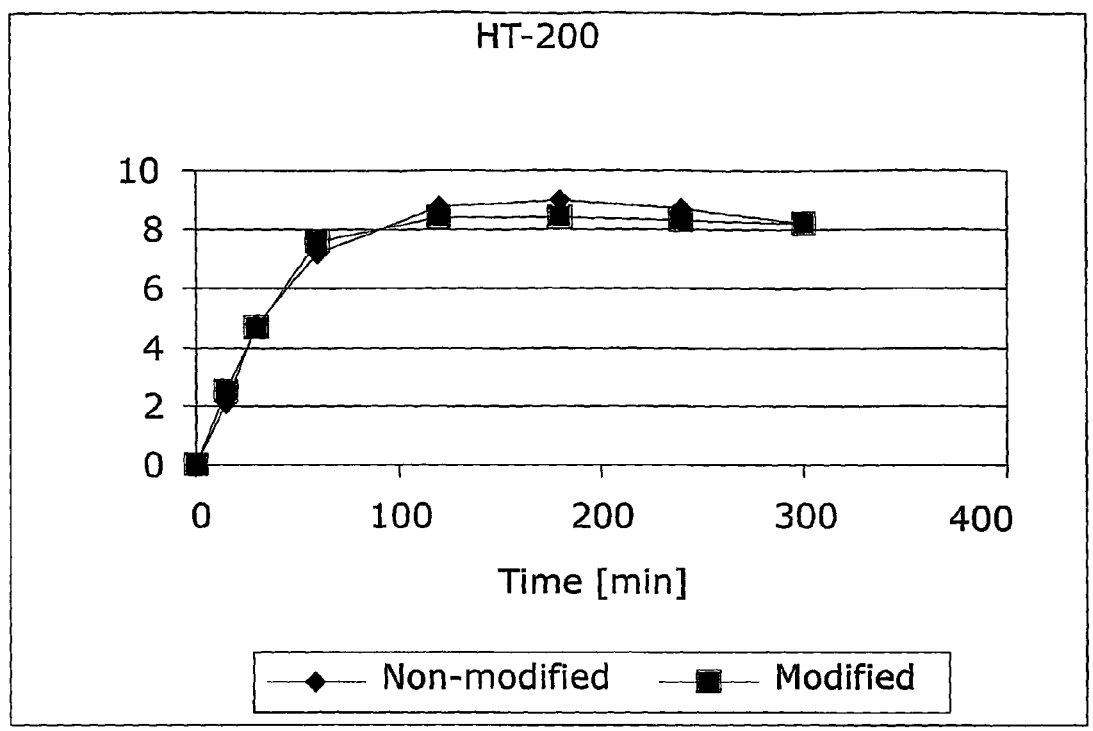
FIG. 7a is a diagram comparing dialysis of glucose through a HT 200 membrane with or without titanium coating.
Figure 7B:
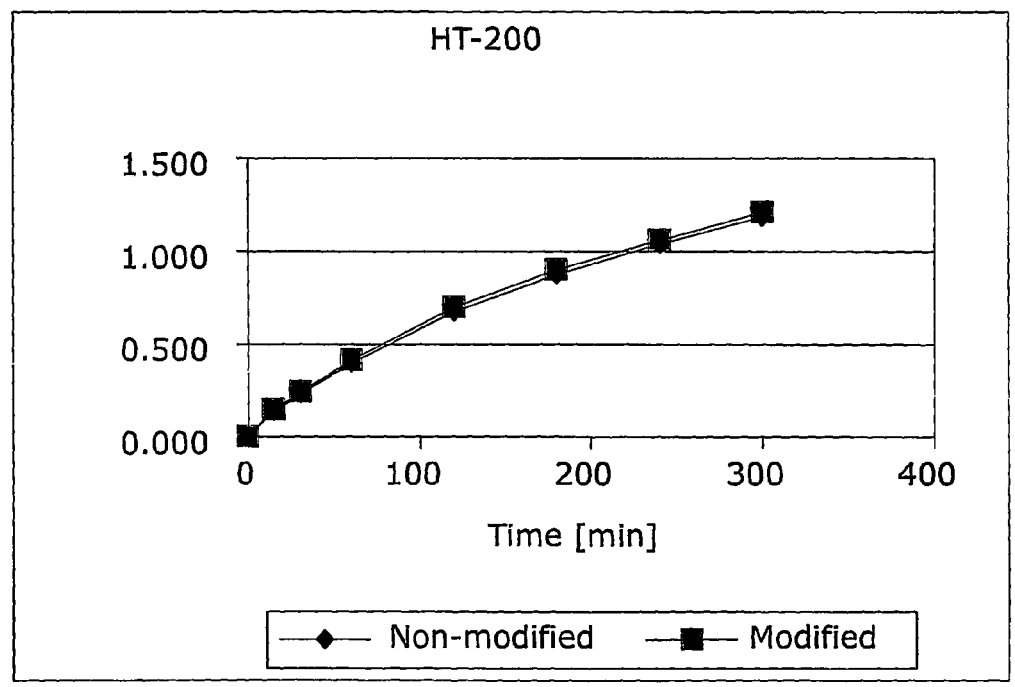
FIG. 7b is a diagram comparing dialysis of protein through a HT 200 membrane with or without titanium coating.
Figure 7C:
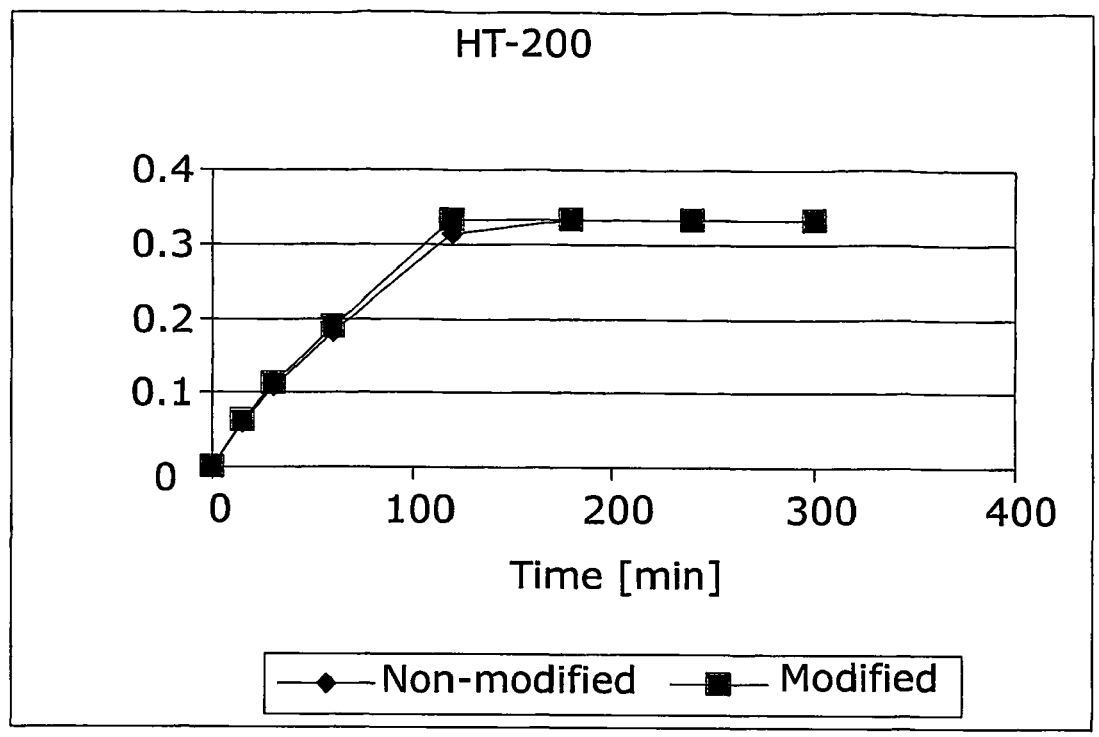
FIG. 7c is a diagram comparing dialysis of IgG through a HT 200 membrane with or without titanium coating.

FIGS. 6a-6d and 7a-7c illustrate dialysis performance, using Versapor® 200 and HT-200 membranes from Pall Corporation. FIG. 6a illustrates the set-up of the dialysis performance test, with a beaker 10, a dialysis chamber 11, a membrane 12 and a magnetic stirrer 13. The dialysis chamber 11 was filled with 1 ml human blood containing 0.5 M glucose and 2.5 U/L insulin and the membrane was assembled onto the chamber. Dialysis was performed in a beaker filled with 50 ml PBS. Samples were collected at 0, 15, 30, 60, 120, 180, 240 and 300 min and were analyzed for absorbance at 280 nm showing glucose concentration, proteins concentration and IgG content. No difference in dialysis performance could be found between non-coated and Ti-coated Versapor® 200 and HT 200 membranes. FIG. 6b illustrates dialysis of glucose through Versapor® 200 membrane, FIG. 6c illustrates dialysis of proteins through Versapor® 200 membrane and FIG. 6d illustrates dialysis of IgG through Versapor® 200 membrane. FIG. 7a illustrates dialysis of glucose through the HT-200 membrane, FIG. 7b illustrates dialysis of proteins through the HT-200 membrane and FIG. 7c illustrates dialysis of IgG through the HT-200 membrane.

EXAMPLE 8

Figure 8A:
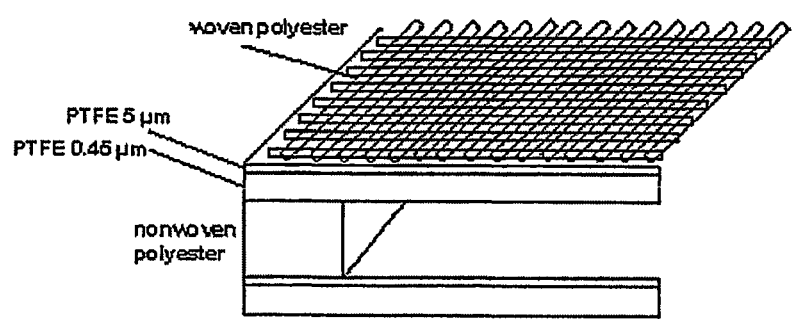
FIG. 8a is a schematic illustration of a TheraCyte™ device.

A TheraCyte™ device, see FIG. 8a, is basically a bag formed between two sheets of membranes. Each sheet is built up of three layers, one outer layer of woven polyester, a middle layer of PTFE with 5 μm pore size and an inner layer of PTFE with 0.45 μm pore size. The two outer layers are supposed to work as a guide for blood vessel formation. The inner layer is an isolating layer to isolate the inside from outside cells.

The above TheraCyte™device was studied before and after coating with one or two Ti-layers, using a LEICA M76 microscope with an external light source and a Nikon Eclipse E600 light microscope. No change in device-structure due to the Ti-coating procedure could be observed. FIG. 8b illustrates the device without modification (no Ti-coating), FIG. 8c illustrates the device with one Ti-layer, and FIG. 8d illustrates the device with two Ti-layers. FIGS. 8e, 8h, 8k illustrate the device without modification, FIGS. 8f, 8i, 8l illustrates the device with one Ti-layer and FIGS. 8g, 8j, 8m illustrates the device with two Ti-layers, respectively.

Dialysis was performed with the above devices in 0.9% NaCl. Insulin and radioactively labeled glucose, respectively, were introduced in the device. Samples were collected at 0, 15, 30, 60, 120 and 180 minutes after the start of dialysis. Glucose was detected using a liquid scintillation counter, and insulin using IsoInsulin Enzyme ImmunoAssay (EIA).

Figure 8N:
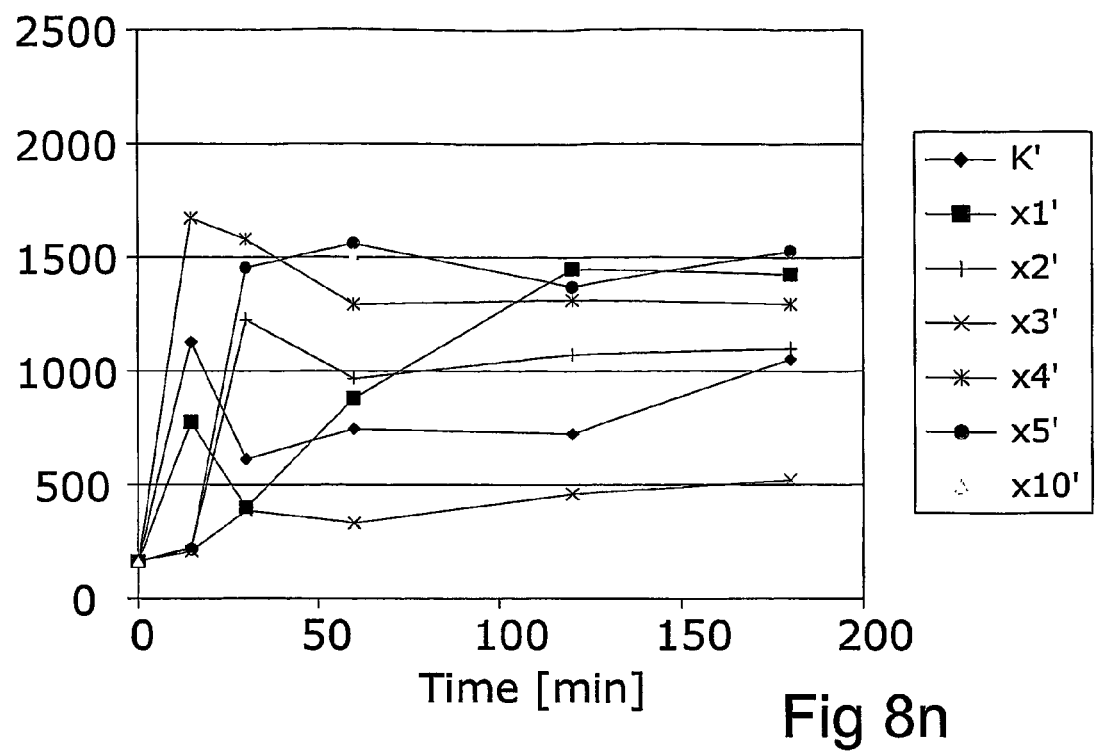
FIG. 8n is a diagram illustrating dialysis of glucose from a TheraCyte™ device with no titanium coating (K) or with 1-5 or 10 titanium layers coated onto the device.
Figure 8O:
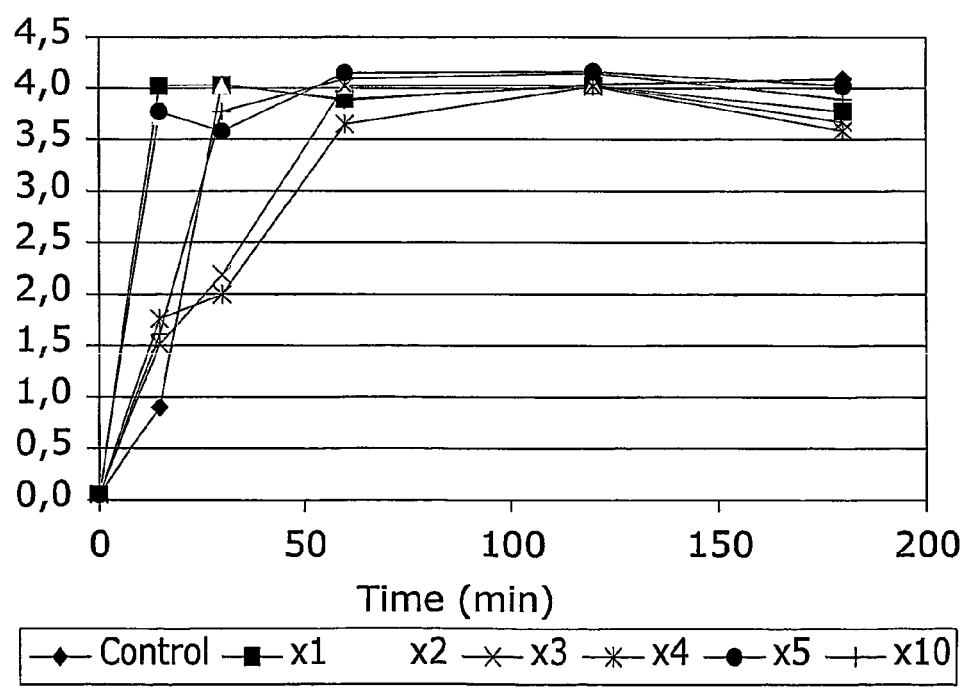
FIG. 8o is a diagram illustrating dialysis of insulin from a TheraCyte™ device with no titanium coating (control) or with 1-5 or 10 titanium layers coated onto the device.

Result: see FIGS. 8n and 8o. FIG. 8n illustrates dialysis of glucose from the TheraCyte™ device. The number indicates the number of Ti-layers coated onto the device. K indicates a non-modified device. FIG. 8o illustrates dialysis of insulin from the TheraCyte™ device. The number indicates the number of layers coated onto the device. Control indicates a non-modified device.

Figures 8P, 8Q, 8R, 8S:
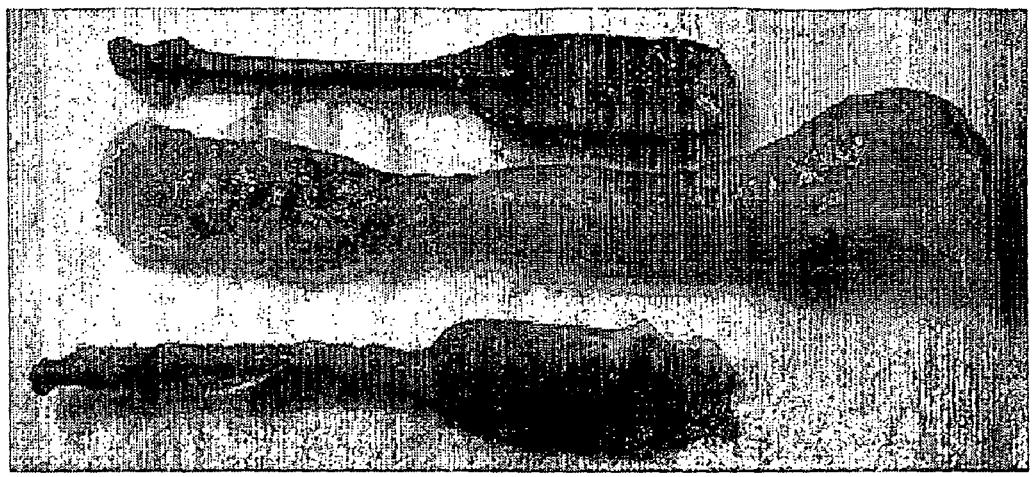
FIGS. 8p-8s illustrate TheraCyte™ devices with two titanium layers (top, FIG. 8p), no titanium coating (middle, FIG. 8r) or a single titanium layer (bottom, FIG. 8s) after 17 days of implantation in male LEWIS rats.
Figure 8T:
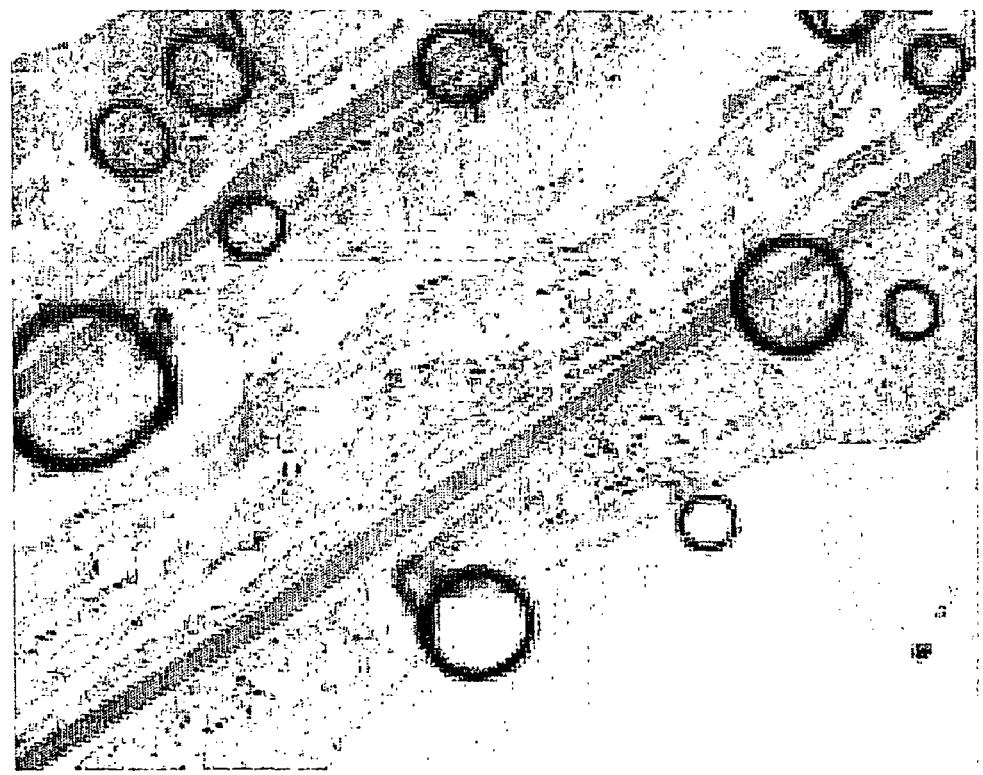
FIG. 8t is cross-sectional view of the control TheraCyte™ device illustrated in FIG. 8r.
Figure 8U:
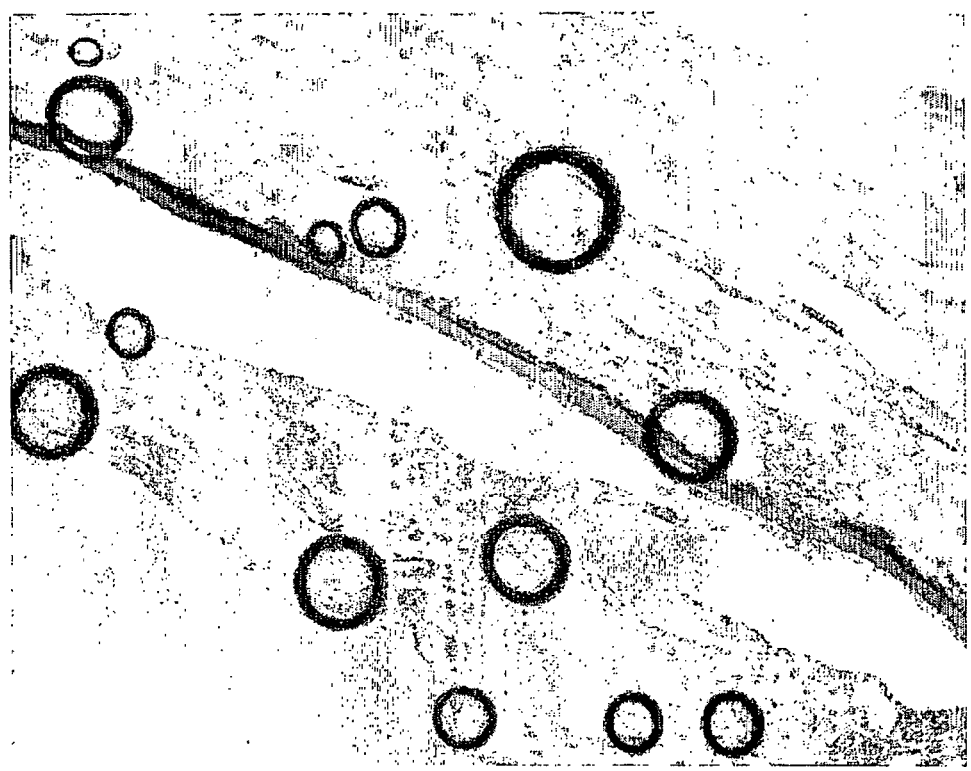
FIG. 8u is cross-sectional view of the TheraCyte™ device with a single titanium layer illustrated in FIG. 8s.
Figure 8V:
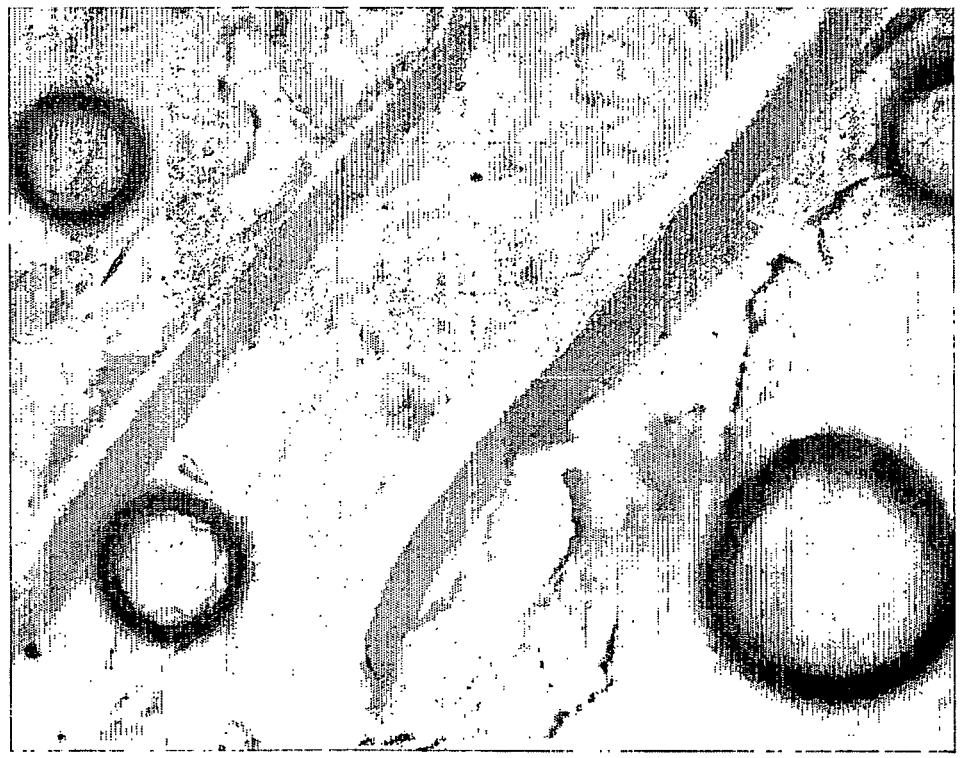
FIG. 8v is cross-sectional view of the TheraCyte™ device with two titanium layers illustrated in FIG. 8p.

TheraCyte™ devices were implanted in male LEWIS rats. After 17 days the devices were removed. On a macroscopic level the non-coated device is surrounded by a capsule containing sera liquid. Cross-sections reveal the existence of a tighter tissue contact for the Ti-coated TheraCyte™ device than the non-coated device. See FIGS. 8p-8s, from top: FIG. 8p two Ti-layers, FIG. 8r control (non-coated, non-modified), FIG. 8s a single Ti-layer. FIG. 8t illustrates a cross-section of the control device (non-modified, no Ti-coating), FIG. 8u illustrates a cross-section of the device with one Ti-layer and FIG. 8v illustrates a cross-section of the device with two Ti-layers.

Figures 9A, 9B:
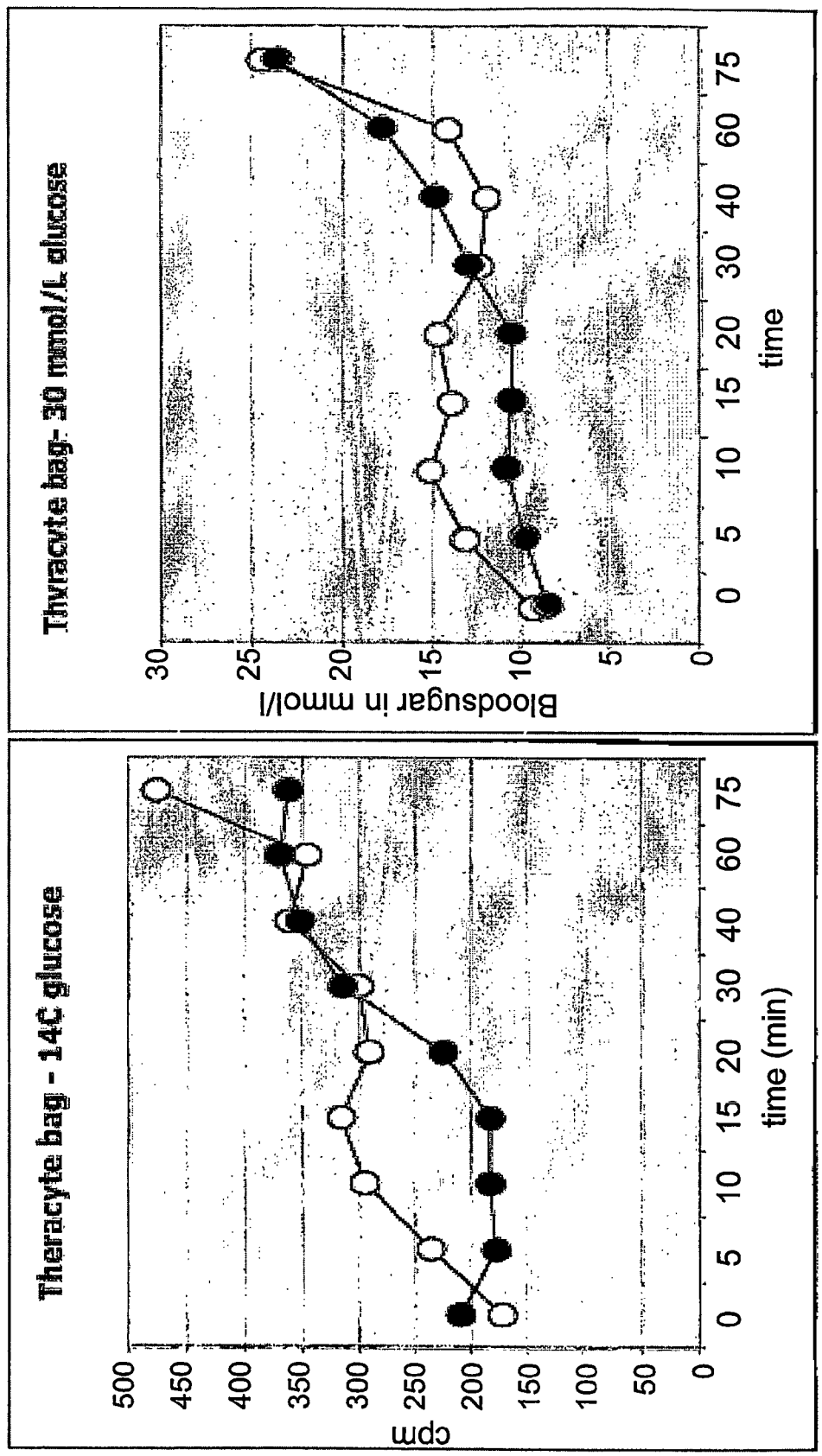
FIG. 9a is a diagram illustrating measured radioactivity from blood drawn from mice having implanted TheraCyte™ devices into which $^{14}$C-glucose was injected 41 days after implantation, closed circles represent devices with no titanium coating and open circles represent devices with a titanium coating.
FIG. 9b is a diagram illustrating measured glucose concentration from blood drawn from mice having implanted TheraCyte™ devices into which $^{14}$C-glucose was injected 41 days after implantation, closed circles represent devices with no titanium coating and open circles represent devices with a titanium coating.

FIGS. 9a and 9b illustrate TheraCyte™ bags implanted into mice under the pectoralis muscles. The bags were left in the animal for 41 days and thereafter a 30 mMol/L glucose solution containing $^{14}C$-glucose was injected into the bags. Blood samples were drawn as indicated in FIG. X. The figure demonstrates that the glucose level, as reflected both by the actual concentration and the radioactivity, is constant at about 10 mmol/L until 20 min followed by an increase up to 25 mmol/L after 75 min in the control animal with an uncoated bag (closed circles). By contrast, the glucose levels start to rise already after 5 min in the animals which have received a bag with a titanium coat.

This result is fully in agreement with the finding that the titanium coat gives a much tighter bond to the surrounding tissue, thereby allowing glucose to diffuse directly into the tissues and the surrounding blood vessels. By contrast, in the control animal the contact between the bag and the tissue is not tight, which creates a slit between the material and the tissue and a fibrous tissue capsule. Glucose has to diffuse into the fluid of the slit and the fibrous tissue capsule before it reaches the vessels of the tissue. This explains the delay in the increase of the glucose concentration.

Figure 10:
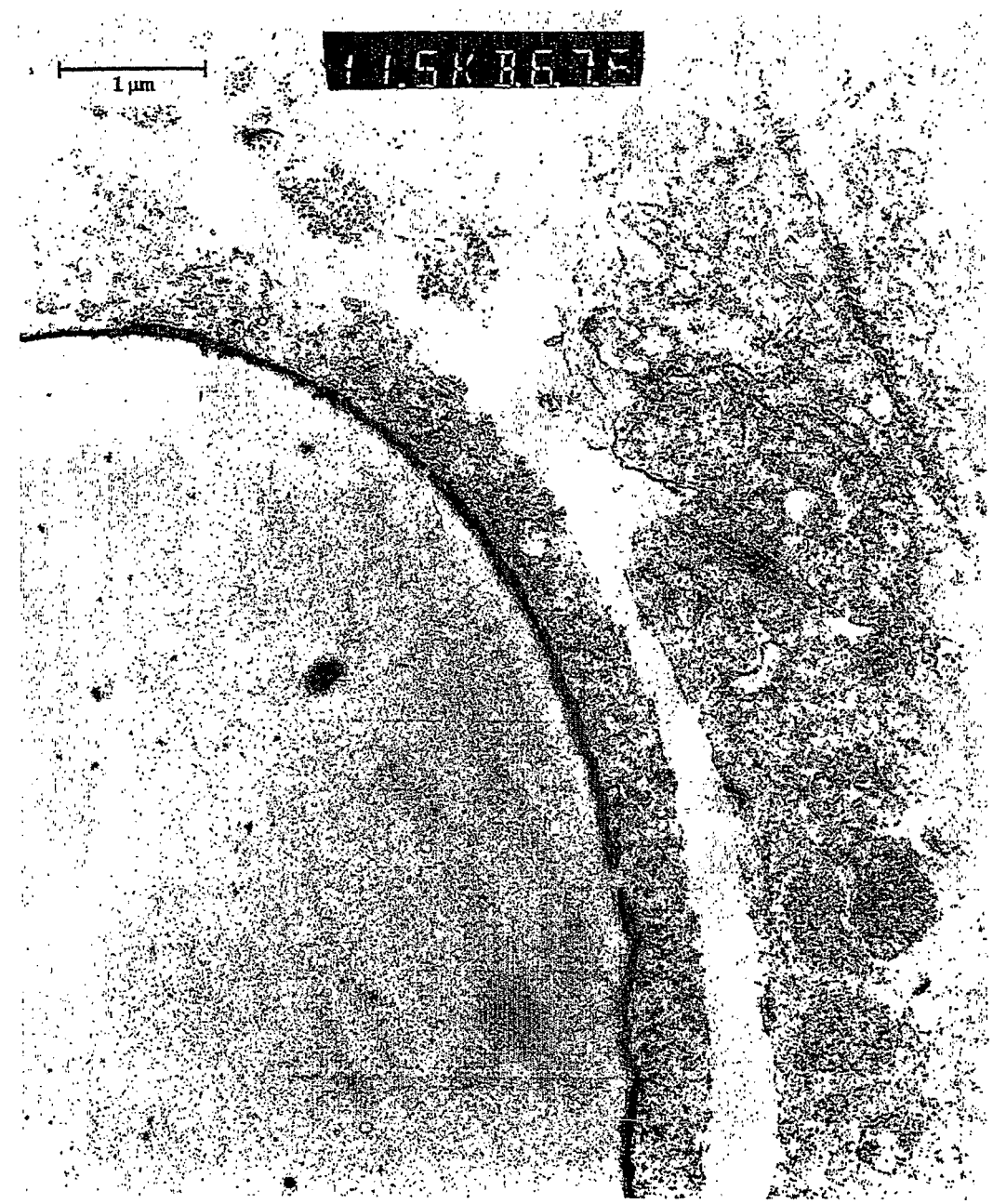
FIG. 10 is an electron microscopy image of an implanted titanium-coated TheraCyte™ device in 115000 magnification.

FIG. 10 illustrates part of an implanted TheraCyte™ bag in an electron microscope, in 11500 magnification. The whitish part to the left is a filament of the woven polyester layer, the black string close thereto is the Ti-coating and the rest is body tissue, closely to the Ti-coating. The Ti-coating is about 100 nm thick.

What the invention claims is:

1. A bioartificial implant, comprising: a semipermeable barrier having a surface coating of a bioactive metal, the surface coating being permeable to not interfere with the semipermeability of the semipermeable barrier, wherein the semipermeable barrier is designed, to allow diffusion of body cell nutrients and oxygen from a donee's body from a first side to a second opposite side of the semipermeable barrier where body organ/cells from a donor are positioned, and from the second opposite side and to the first side to allow diffusion of substances, produced by the donor's body organs and cells.

2. An implant as claimed in claim 1, wherein said surface coating is a net of said bioactive metal.

3. An implant as claimed in claim 1, wherein said bioactive metal is selected from one of titanium, zirconium, tantalum or an alloy thereof.

4. An implant as claimed in claim 3, wherein said bioactive metal is titanium.

5. An implant as claimed in claim 1, wherein the metal is applied by an atomizing process.

6. An implant as claimed in claim 1, wherein the bioartificial implant is in the form of a container.

7. An implant as claimed in claim 1, wherein the semipermeable barrier has said surface coating on both sides.

8. An implant as claimed in claim 1, wherein the coating has a thickness greater than 5 nm.

9. An implant as claimed in claim 8, wherein the coating has a thickness of about 50-250 nm.

10. A bioartificial implant, comprising: a semipermeable barrier having a surface coating of a bioactive metal, the surface coating being permeable to not interfere with the semipermeability of the semipermeable barrier: and a sensor element enclosed by said semipermeable barrier, wherein the semipermeable barrier is designed, from a first side to allow diffusion of a substance to a second opposite side of the semipermeable barrier, the substance being detectable by the sensor element, and from the second opposite side to allow diffusion of the substance to the first side.

11. An implant as claimed in claim 10, wherein said substance is blood sugar and said sensor element is a blood-sugar detecting sensor element.

12. An insulin pump comprising:

a bioartificial implant as claimed in claim 11, and an infusion set for delivering insulin based on a blood sugar level detected by said blood-sugar-detecting sensor element of said bioartificial implant, whereby said infusion set is provided with a semipermeable barrier having a surface coating of said bioactive metal, said surface coating being permeable to allow diffusion of insulin through said semipermeable barrier.

* * * * *

UNITED STATES PATENT AND TRADEMARK OFFICE
CERTIFICATE OF CORRECTION

PATENT NO. : 7,955,613 B2  
APPLICATION NO. : 10/574114  
DATED : June 7, 2011  
INVENTOR(S) : Adam Bruce et al.

Page 1 of 1

It is certified that error appears in the above-identified patent and that said Letters Patent is hereby corrected as shown below:

On the Title Page, Item (56), "Foreign Patent Documents" should be amended to include:

JP 62-500980    4/1987  
JP 2004-528109   9/2004  
JP 2003-530926   10/2003  
JP 7-507550      8/1995  
JP 6-507412      8/1994

Signed and Sealed this  
Tenth Day of July, 2012

David J. Kappos  
*Director of the United States Patent and Trademark Office*